US007988987B2

(12) United States Patent
Ranade

(10) Patent No.: US 7,988,987 B2
(45) Date of Patent: Aug. 2, 2011

(54) MEDICAL DEVICES CONTAINING CRAZED POLYMERIC RELEASE REGIONS FOR DRUG DELIVERY

(75) Inventor: Shrirang V. Ranade, Arlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1474 days.

(21) Appl. No.: 11/042,038

(22) Filed: Jan. 25, 2005

(65) Prior Publication Data
US 2006/0165754 A1 Jul. 27, 2006

(51) Int. Cl.
*A61F 2/02* (2006.01)
(52) U.S. Cl. ...................................... 424/426
(58) Field of Classification Search .................. None
See application file for complete search history.

(56) References Cited

U.S. PATENT DOCUMENTS

| 5,824,048 | A | 10/1998 | Tuch |
| 6,414,050 | B1 * | 7/2002 | Howdle et al. ............... 523/105 |
| 6,419,692 | B1 | 7/2002 | Yang et al. |
| 6,545,097 | B2 | 4/2003 | Pinchuk et al. |
| 2003/0033004 | A1 | 2/2003 | Ishii et al. |
| 2004/0175406 | A1 | 9/2004 | Schwarz |
| 2006/0088567 | A1 | 4/2006 | Warner et al. |

FOREIGN PATENT DOCUMENTS

DE 10063612 7/2002

OTHER PUBLICATIONS

Giacomo Di Colo, "Controlled Drug Release from Implantable Matrices Based on Hydrophobic Polymers," *Biomaterials*, vol. 13 (1992): 850-856.
I.M. Brook et al., "Drug release from acrylic polymers via channels and cracks: In vitro studies with hydrocortisone," *Biomaterials*, vol. 6 (1985): 281-285.
"MBS Impact Modifiers", http://www.specialchem4polymers.com/tc/MBS-Impact-Modifiers/index.aspx?id=crazing, 2 pages, publication date unknown, but prior to the filing date of the instant application.
"3 Deformation Morphologies and Toughening of Polymer Systems", Chapter 8 pp. 349, http://www.eng.uc.edu/~gbeaucg/Classes/Morphology/Chapter3html/Chapter3.html, 7 pages, Apr. 27, 1998.
"Experimental Polymer Physics," Department of Physics & Astronomy, McMaster University, http://physwww.physics.mcmaster.ca/~dalnoki/cgi-bin/display.pl?page=img03, 1 page, publication date unknown, but prior to the filing date of the instant application.
Michler, Goerg H., "Micromechanical Properties," http://www.mrw.interscience.wiley.com/enst/articles/pst199/sect9.html, 6 pages, posted online Oct. 22, 2001.

* cited by examiner

*Primary Examiner* — Carlos Azpuru
(74) *Attorney, Agent, or Firm* — Mayer & Williams PC; David B. Bonham; Keum J. Park

(57) ABSTRACT

A medical device that contains (a) at least one polymeric release region that either contains crazing or which is adapted to undergo crazing as a result of stresses (e.g., mechanical, chemical or thermal) that are applied during the implantation or insertion of the medical device into a patient; and (b) a therapeutic agent disposed beneath or within the polymeric release region.

38 Claims, No Drawings

MEDICAL DEVICES CONTAINING CRAZED POLYMERIC RELEASE REGIONS FOR DRUG DELIVERY

FIELD OF THE INVENTION

The present invention relates generally to medical devices, and more particularly to medical devices which contain polymer regions for release of therapeutic agents.

BACKGROUND OF THE INVENTION

The in vivo delivery of a biologically active agent within the body of a patient is common in the practice of modern medicine. In vivo delivery of biologically active agents is often implemented using medical devices that may be temporarily or permanently placed at a target site within the body. These medical devices can be maintained, as required, at their target sites for short or prolonged periods of time, delivering biologically active agents at the target site.

For example, numerous polymer-based medical devices have been developed for the delivery of therapeutic agents to the body. Examples include drug eluting coronary stents, which are commercially available from Boston Scientific Corp. (TAXUS), Johnson & Johnson (CYPHER), and others.

In accordance with some typical delivery strategies, a therapeutic agent is provided within or beneath a biostable or biodisintegrable polymeric layer that is associated with a medical device. Once the medical device is placed at the desired location within a patient, the therapeutic agent is released from the medical device with a profile that is dependent, for example, upon the loading of the therapeutic agent and upon the nature of the polymeric layer.

Controlling the rate of therapeutic agent release and the overall dose are key parameters for proper treatment in many cases. Selection of the polymeric layer will have a great impact on these parameters. In many formulations, the thickness of the layer can be changed to control the total dose. Nonetheless, the therapeutic agent becomes trapped in the release layer in many instances, never to be released.

SUMMARY OF THE INVENTION

These and other challenges addressed by the present invention which, in one aspect, provides a medical device that contains (a) at least one polymeric release region that either contains crazing or which is adapted to undergo crazing as a result of stresses that are applied during the implantation or insertion of the medical device into a patient; and (b) and a therapeutic agent disposed beneath or within the polymeric release region.

An advantage of the present invention is that medical devices can be provided in which the rate of therapeutic agent release is increased.

Another advantage of the present invention is that medical devices can be provided in which the amount of trapped therapeutic agent is reduced.

These and other embodiments and advantages of the present invention will become immediately apparent to those of ordinary skill in the art upon review of the Detailed Description and Claims to follow.

DETAILED DESCRIPTION OF THE INVENTION

A more complete understanding of the present invention is available by reference to the following detailed description of numerous aspects and embodiments of the invention. The detailed description of the embodiments which follows is intended to illustrate but not limit the invention. The scope of the invention is defined by the appended claims.

As indicated above, in one aspect, the present invention provides a medical device that contains (a) at least one polymeric release region that either contains crazing or which is adapted to undergo crazing as a result of stresses that are applied during the implantation or insertion of the medical device into a patient; and (b) and a therapeutic agent disposed beneath or within the polymeric release region.

Examples of medical devices to which the present invention is applicable include a wide variety of implantable or insertable medical devices, for example, catheters (e.g., renal or vascular catheters such as balloon catheters), guide wires, balloons, filters (e.g., vena cava filters), stents (including coronary artery stents, peripheral vascular stents such as cerebral stents, urethral stents, ureteral stents, biliary stents, tracheal stents, gastrointestinal stents and esophageal stents, which may be, for example, non-expandable, self-expanding or mechanically expandable), stent grafts, cerebral aneurysm filler coils (including Guglilmi detachable coils and metal coils), vascular grafts, myocardial plugs, pacemaker leads, heart valves, vascular valves, tissue engineering scaffolds for cartilage, bone, skin and other in vivo tissue regeneration, sutures, suture anchors, anastomosis clips and rings, tissue staples and ligating clips at surgical sites, as well as various other medical devices that are adapted for implantation or insertion into the body. In certain embodiments, the medical device is an expandable medical device.

The medical devices of the present invention include implantable and insertable medical devices that are used for systemic treatment and those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Preferred subjects (also referred to as "patients") are vertebrate subjects, more preferably mammalian subjects and more preferably human subjects.

Specific examples of medical devices for use in conjunction with the present invention include vascular stents, such as coronary stents and cerebral stents, which deliver a therapeutic agent into the vasculature for the treatment of restenosis.

In some embodiments, the polymeric release regions of the present invention correspond to an entire medical device. In other embodiments, the polymeric release regions correspond or to one or more portions of a medical device. For instance, the polymeric release regions can be in the form of one or more fibers which are incorporated into a medical device, in the form of one or more polymeric layers formed over all or only a portion of an underlying medical device substrate, and so forth. Layers can be provided over an underlying substrate at a variety of locations, and in a variety of shapes, and they can be formed from a variety of polymeric materials. Materials for use as underlying medical device substrates include ceramic, metallic and polymeric substrates. The substrate material can also be formed using a carbon- or silicon-based material. As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

Release regions in accordance with the present invention include carrier regions and barrier regions. By "carrier region" is meant a release region which further comprises a therapeutic agent and from which the therapeutic agent is released. For example, in some embodiments, the carrier region constitutes the entirety of the medical device (e.g., provided in the form of a stent body). In other embodiments, the carrier region corresponds on only a portion of the device (e.g., e.g., a coating overlying a medical device substrate such as a stent body). By "barrier region" is meant a region which is disposed between a source of therapeutic agent and a site of intended release, and which controls the rate at which therapeutic agent is released. For example, in some embodiments, the medical device consists of a barrier region that surrounds a source of therapeutic agent. In other embodiments, the barrier region is disposed over a source of therapeutic agent, which is in turn disposed over all or a portion of a medical device substrate.

As noted above, the present invention is directed to medical devices in which polymeric release regions area subjected to crazing. Crazing is a phenomenon found in most amorphous glassy plastics as well as in other polymers, including certain semi-crystalline polymers.

Crazes are made up of microscopic elongated voids, which have the appearance of being microscopic cracks. However, unlike cracks, crazes are bridged by elongated polymeric regions called fibrils. Because voids are formed, crazing results in an increase in the volume of the material. This means that a crazed polymer is of lower density than its un-crazed polymer counterpart. This also means that that crazing generally occurs under conditions of stress where there is a force component that leads to an increase in volume, either throughout the polymeric release region or in only a portion thereof (e.g. under the application of tensile stresses, which have a tendency to pull the polymer molecules apart from one another). The voids are known to form in a plane that is perpendicular to the direction of the stress, and the fibrils are parallel to the direction of stress, stabilizing the voids. In addition to mechanical stresses, solvents (e.g., water and/or organic solvents), plasticizers, compatibilizers or other media that expand the volume of polymeric regions (e.g., by swelling the polymer) are also known to cause crazing, as are thermal stresses (e.g. stresses from rapidly heating the material). In addition, combinations of two or more of the above (i.e., mechanical, chemical, thermal) processes can also clearly be used to create crazing.

Crazes are ordinarily considered undesirable. For example, although crazes are not a sign of failure, crazing is often a precursor to crack growth, which can lead eventually to failure. In the present invention, however, crazing is used to assist with drug delivery from the polymer, and it is therefore desirable. Without wishing to be bound by theory, it is believed that by virtue their associated voids, crazes render the interior of the polymeric release region of the medical device more accessible to biological fluids. Moreover, in biodegradable polymers that craze, the crazes can also be used to increase the rate of degradation of the polymer and thus increase the release of therapeutics (e.g., due to increased access to biological fluids). Consequently, crazing is expected increase the rate at which the therapeutic agent is released from the polymeric release regions of the present invention. In biostable polymeric release regions, crazing is also expected to increase the total amount of therapeutic agent that is released (thereby reducing the amount of drug that ultimately remains in the device, improving delivery efficiency). This is in contrast, for example, to biostable polymeric release regions that do not form crazes, in which therapeutic agent is commonly trapped, unable to be eluted from the device. Such trapping issues are particularly acute for high molecular weight therapeutic agents such as polysaccharides, polypeptides (e.g., proteins) or polynucleotides (e.g., plasmid DNA). Thus the present invention is advantageous in that it provides a mechanism for increasing the rate and/or cumulative amount of therapeutic agent that is released.

The release profile of therapeutic agent can also be dictated by properties of the polymeric release regions other than their tendencies to craze, such as their biostability/biodegradability, their relative hydrophilicity/hydrophobicity, and so forth.

The release profile can also be modified by changing the size, number or position of the polymeric release regions within the device. For example, the release profile of polymeric carrier and barrier layers in accordance with the presenting invention can be modified by varying the thickness or surface areas of the same. Moreover, multiple polymeric release regions can be employed to modify the release profile. For example, multiple carrier or barrier layers of the invention, either having the same or different content (e.g., different polymer and/or therapeutic agent content), can be stacked on top of one another, can be positioned laterally to one another, and so forth.

In general, crazes within the polymeric release regions of present invention are formed either ex vivo or in vivo.

For example, in some aspects of the invention, a medical device having a polymeric release region which is adapted to undergo crazing upon exertion of mechanical stress is administered to a patient. Mechanical stresses are exerted on the polymeric release region in vivo, leading to the formation of crazes. An example of a situation where craze-inducing forces are exerted at the time of device implantation or insertion is the case where the polymeric release region corresponds to a balloon or to a portion thereof (e.g., a balloon coating). Another example is the case where the polymeric release region corresponds to a stent or a portion thereof (e.g., a stent coating). In cases where the polymeric release region is provided as a coating layer over a metallic stent body, various mechanically expandable (e.g., balloon expandable) and self-expandable materials are presently used in stents, such as nickel-titanium alloys, stainless steel and cobalt alloys, which undergo deformation (including elongation) during expansions and will therefore exert stresses (including tensile stresses) on an overlying coating.

In other embodiments of the invention, a crazed polymeric release region is formed ex vivo, for example, by methods in which stresses are applied mechanically to induce crazing, in which stresses are created thermally, and/or by methods in which one or more species (e.g., solvents, plasticizers, compatibilizers, etc.) are applied which act to swell the polymeric release region and induce crazing. With respect to solvent swelling, the solvent system used will vary depending on the composition of the polymeric release region, and can be selected from aqueous solvents, organic solvents (which contain one or more organic solvent species), and aqueous/organic solvents (which contain water and one or more organic solvent species).

Where the crazing is produced ex vivo, the polymeric release region can be first formed and subsequently attached to another medical device portion, or the ex vivo processing can be performed on a polymeric release region that is already fully associated with a medical device (e.g., where the polymeric release region corresponds to the entire medical device or where the polymeric release region corresponds to a portion of a medical device, for instance, a coating on an underlying substrate).

In certain embodiments where crazing is produced ex vivo, the therapeutic agent is introduced into the polymeric release region subsequent to crazing (e.g., by spraying or imbibing with a solution containing a therapeutic agent as discussed below).

In certain other embodiments, the therapeutic agent is present during the process of ex vivo crazing. Where solvent swelling is utilized, the selected solvent may be poor solvent for the therapeutic agent (e.g., to the extent that it is desirable to minimize therapeutic agent migration).

Regardless of the technique by which the crazing is created, subsequent to implantation, bodily fluids will commonly produce additional crazing over time. For example, the bodily fluids will swell certain polymeric release regions, causing crazing as discussed above. As another example, bodily fluids will also chemically attack the polymer (e.g., due to hydrolysis or enzymatic attack), which may increase mechanical stresses at certain points within the polymeric release region and lead to further crazing. In this regard, it is noted that while chemical attack obviously occurs with biodisintegrable materials, but it also occurs to some degree with biostable materials as well.

As used herein a "polymeric release region" is region that comprises at least 50 wt % polymers, typically at least 75 wt % polymers, and more typically at least 90 wt % polymers.

As used herein, "polymers" are molecules that contain one or more chains, each containing multiple copies of one or more constitutional units. An example of a common polymer chain is polystyrene

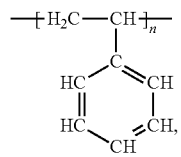

where n is an integer, typically an integer of 10 or more, more typically on the order of 10's, 100's, 1000's or even more, in which the chain contains styrene monomers

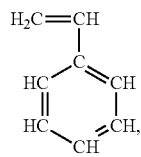

(i.e., the chain originates from, or has the appearance of originating from, the polymerization of styrene monomers, in this case, the addition polymerization of styrene monomers).

Polymers for use in the polymeric release regions of the present invention include homopolymers and copolymers. As used herein, "homopolymers" are polymers whose chains all contain multiple copies of a single constitutional unit. "Copolymers" are polymers, whose chains contain multiple copies of at least two dissimilar constitutional units. Examples include random copolymers, statistical copolymers, gradient copolymers, periodic copolymers (e.g., alternating copolymers), and block copolymers.

Polymers for use in the polymeric release regions of the present invention can have a variety of configurations, including cyclic, linear and branched configurations. Branched configurations include star-shaped configurations (e.g., configurations in which three or more chains emanate from a single branch point), comb configurations (e.g., configurations having a main chain and a plurality of side chains) and dendritic configurations (e.g., arborescent and hyperbranched polymers), among others.

Polymers for use in the polymeric release regions of the present invention include biostable and biodisintegrable polymers. By "biodisintegrable polymer" is meant that the polymer undergoes dissolution, degradation (i.e., bond cleavage, such as hydrolysis) and/or other disintegration process during the time over which the medical device is designed to reside in the body, which can be on the order of months or even years. By "biostable polymer" is meant that the polymer remains substantially intact during the time over which the medical device is designed to reside in the body.

In some embodiments, the polymeric release regions of the present invention are formed using a single type of homopolymer or a single type of copolymer. In some embodiments, the polymeric release regions of the present invention contain a blend two or more types of polymers, for example, (a) two or more homopolymers, (b) two or more copolymers, or (c) a combination of one or more homopolymers and one or more copolymers.

As noted above, crazing is a phenomenon found in most amorphous glassy plastics and in other polymers as well, including certain semi-crystalline polymers. Crazing generally occurs under conditions of stress where there is a force component that leads to an increase in volume throughout the polymeric release region, or in only a portion thereof, for example, by the application of mechanical tensile stresses or solvent swelling, which have a tendency to pull the polymer molecules apart from one another.

Crazing also generally occurs (a) at temperatures below the glass transition temperature of the polymeric release region or (b) where the region has more than one glass transition temperature, at temperatures below at least one glass transition temperature, and preferably all glass transitions temperatures, of the polymeric release region. Glass transition temperature ($T_g$) can be measured by any of a number of techniques including differential scanning calorimetry (DSC), dynamic mechanical analysis (DMA), or dielectric analysis (DEA).

In this connection, the polymers for use in the present invention are typically selected at least in part based on their $T_g$'s.

For example, in some embodiments where crazing is created during device implantation or insertion, a polymeric release region is typically selected, which has a $T_g$ above body temperature (i.e., 37° C.) (or where the polymeric release region has more than one $T_g$, it has at least one $T_g$, and preferably all $T_g$·s above body temperature), more typically between 5 and 80° C. above body temperature. However, this need not be the case, as it is possible, for example, to cool the polymeric release region to some degree during the process of device implantation or insertion.

Similarly, in embodiments where crazing of the polymeric release region is brought about ex vivo, a polymeric release region is typically selected, which has a $T_g$ above processing temperature (or where the polymeric release region has more than one $T_g$, it has at least one $T_g$, and preferably all $T_g$·s, above processing temperature), more typically between 5 and 80° C. above processing temperature. Hence, in various embodiments, it may be desirable to conduct processing at sub-ambient temperatures.

Using the above criteria, a wide a variety of polymers can be used in the polymeric release regions of the present invention. Examples of polymers for forming the polymeric release regions of the present invention include homopolymers and copolymers, which contain one or more chains having a $T_g$ above body temperature (where the crazing is produced in vivo) or which contain one or more chains having a $T_g$ above crazing temperature (wherein the crazing is produced ex vivo). Specific examples of polymer chains include homopolymer and copolymer chains formed from (or having the appearance of being formed from) one or more of the following: vinyl aromatic monomers, other vinyl monomers (besides vinyl aromatic monomers), other aromatic monomers (besides vinyl aromatic monomers), methacrylic monomers, acrylic monomers, and alkene monomers.

Vinyl aromatic monomers are those having aromatic and vinyl moieties and include unsubstituted monomers, vinyl-substituted monomers and ring-substituted monomers. Specific vinyl aromatic monomers include the following (published $T_g$.s for the corresponding homopolymer are shown in parentheses): (a) unsubstituted vinyl aromatics, such as atactic styrene ($T_g$ 100° C.), isotactic styrene ($T_g$ 100° C.) and 2-vinyl naphthalene ($T_g$ 151° C.), (b) vinyl substituted aromatics such as α-methyl styrene, (c) ring-substituted vinyl aromatics including (i) ring-alkylated vinyl aromatics such as 3-methylstyrene ($T_g$ 97° C.), 4-methylstyrene ($T_g$ 97° C.), 2,4-dimethylstyrene ($T_g$ 112° C.), 2,5-dimethylstyrene ($T_g$ 143° C.), 3,5-dimethylstyrene ($T_g$ 104° C.), 2,4,6-trimethylstyrene ($T_g$ 162° C.), and 4-tert-butylstyrene ($T_g$ 127° C.), (ii) ring-alkoxylated vinyl aromatics, such as 4-methoxystyrene ($T_g$ 113° C.) and 4-ethoxystyrene ($T_g$ 86° C.), (iii) ring-halogenated vinyl aromatics such as 2-chlorostyrene ($T_g$ 119° C.), 3-chlorostyrene ($T_g$ 90° C.), 4-chlorostyrene ($T_g$ 110° C.), 2,6-dichlorostyrene ($T_g$ 167° C.), 4-bromostyrene ($T_g$ 18° C.) and 4-fluorostyrene ($T_g$ 95° C.) and (iv) ester-substituted vinyl aromatics such as 4-acetoxystyrene ($T_g$ 116° C.).

Specific other vinyl monomers include the following: (a) vinyl alcohol ($T_g$ 85° C.); (b) vinyl esters such as vinyl benzoate ($T_g$ 71° C.), vinyl 4-tert-butyl benzoate ($T_g$ 101° C.), vinyl cyclohexanoate ($T_g$ 76° C.), vinyl pivalate ($T_g$ 86° C.), vinyl trifluoroacetate ($T_g$ 46° C.), vinyl butyral ($T_g$ 49° C.), (c) vinyl amines such as 2-vinyl pyridine ($T_g$ 104° C.), 4-vinyl pyridine ($T_g$ 142° C.), and vinyl carbazole ($T_g$ 227° C.), (d) vinyl halides such as vinyl chloride ($T_g$ 81° C.) and vinyl fluoride ($T_g$ 40° C.); (e) alkyl vinyl ethers such as methyl vinyl ether ($T_g$ −31° C.), propyl vinyl ether ($T_g$ −49° C.), butyl vinyl ether ($T_g$ −55° C.), isobutyl vinyl ether ($T_g$ −19° C.), tert-butyl vinyl ether ($T_g$ 88° C.) and cyclohexyl vinyl ether ($T_g$ 81° C.), and (f) other vinyl compounds such as 1-vinyl-2-pyrrolidone ($T_g$ 54° C.) and vinyl ferrocene ($T_g$ 189° C.).

Specific other aromatic monomers, other than vinyl aromatics, include acenaphthalene ($T_g$ 214° C.) and indene ($T_g$ 85° C.).

Specific methacrylic monomers include (a) methacrylic acid ($T_g$ 228° C.), (b) methacrylic acid salts such as sodium methacrylate ($T_g$ 310° C.), (c) methacrylic acid anhydride ($T_g$ 159° C.), (d) methacrylic acid esters (methacrylates) including (i) alkyl methacrylates such as atactic methyl methacrylate ($T_g$ 105-120° C.), syndiotactic methyl methacrylate ($T_g$ 115° C.), ethyl methacrylate ($T_g$ 65° C.), isopropyl methacrylate ($T_g$ 81° C.), butyl methacrylate ($T_g$ 20° C.), isobutyl methacrylate ($T_g$ 53° C.), t-butyl methacrylate ($T_g$ 118° C.), hexyl methacrylate ($T_g$ −5° C.), cyclohexyl methacrylate ($T_g$ 92° C.), 2-ethylhexyl methacrylate ($T_g$ −10° C.), octyl methacrylate ($T_g$ −20° C.), dodecyl methacrylate ($T_g$ −65° C.), hexadecyl methacrylate ($T_g$ 15° C.) and octadecyl methacrylate ($T_g$ −100° C.), (ii) aromatic methacrylates such as phenyl methacrylate ($T_g$ 100° C.) and including aromatic alkyl methacrylates such as benzyl methacrylate ($T_g$ 54° C.), (iii) hydroxyalkyl methacrylates such as 2-hydroxyethyl methacrylate ($T_g$ 57° C.) and 2-hydroxypropyl methacrylate ($T_g$ 76° C.), (iv) aminoalkyl methacrylates such as diethylaminoethyl methacrylate ($T_g$ 20° C.) and 2-tert-butyl-aminoethyl methacrylate ($T_g$ 33° C.), (v) additional methacrylates including isobornyl methacrylate ($T_g$ 110° C.) and trimethylsilyl methacrylate ($T_g$ 68° C.), and (e) other methacrylic-acid derivatives including methacrylonitrile ($T_g$ 120° C.).

Specific acrylic monomers include (a) acrylic acid ($T_g$ 105° C.), its anhydride and salt forms, such as potassium acrylate ($T_g$ 194° C.) and sodium acrylate ($T_g$ 230° C.); (b) certain acrylic acid esters, including alkyl acrylates, arylalkyl acrylates, alkoxyalkyl acrylates, halo-alkyl acrylates and cyanoalkyl acrylates, such as alkyl acrylates such as methyl acrylate ($T_g$ 110° C.), ethyl acrylate ($T_g$ −24° C.), n-propyl acrylate, isopropyl acrylate ($T_g$ −11° C.), butyl acrylate ($T_g$ −54° C.), sec-butyl acrylate ($T_g$ −26° C.), isobutyl acrylate ($T_g$ −24° C.), tert-butyl acrylate ($T_g$ 43-107° C.), hexyl acrylate ($T_g$ 57° C.), cyclohexyl acrylate ($T_g$ 19° C.), 2-ethylhexyl acrylate ($T_g$ −50° C.), dodecyl acrylate ($T_g$ −3° C.), hexadecyl acrylate ($T_g$ 35° C.), benzyl acrylate ($T_g$ 6° C.), 2-ethoxyethyl acrylate ($T_g$ −50° C.), 2-methoxyethyl acrylate ($T_g$ −50° C.), 2,2,2-trifluoroethyl acrylate ($T_g$ −10° C.), 2-cyanoethyl acrylate ($T_g$ 4° C.) and isobornyl acrylate ($T_g$ 94° C.); (c) acrylic acid amides such as acrylamide ($T_g$ 165° C.), N-isopropylacrylamide ($T_g$ 85-130° C.) and N,N dimethylacrylamide ($T_g$ 89° C.); and (d) other acrylic-acid derivatives including acrylonitrile ($T_g$ 125° C.).

Specific alkene based monomers include the following: ethylene (HDPE) ($T_g$ −125° C.), isotactic propylene ($T_g$ −8° C.), isobutylene ($T_g$ −73° C.), 1-butene ($T_g$ −24° C.), trans-butadiene ($T_g$ −58° C.), 4-methyl pentene ($T_g$ 29° C.), 1-octadecene ($T_g$ 55° C.), 1-octene ($T_g$ −63° C.) and other α-olefins, cis-isoprene ($T_g$ −63° C.), and trans-isoprene ($T_g$ −66° C.) and halogenated alkene monomers including vinylidene chloride ($T_g$ −18° C.), vinylidene fluoride ($T_g$ −40° C.), cis-chlorobutadiene ($T_g$ −20° C.), trans-chlorobutadiene ($T_g$ −40° C.) and tetrafluoroethylene ($T_g$ 117° C.).

Still other polymers for use in the release regions of the present invention can be selected from suitable members of the following: polymers and copolymers of vinyl monomers including polyvinyl alcohols, polyvinyl ketones, polyvinylcarbazoles, polyvinyl esters such as polyvinyl acetates, polyvinyl halides such as polyvinyl chlorides, ethylene-vinyl acetate copolymers (EVA), polyvinylidene chlorides, polyvinyl ethers such as polyvinyl methyl ethers, polyvinylpyrrolidone, vinyl aromatics such as polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk); silicone polymers and copolymers; poly(carboxylic acid) polymers and copolymers including polyacrylic and polymethacrylic acid, and salts thereof, ethylene-methacrylic acid copolymers and ethylene-acrylic acid copolymers, where some of the acid groups can be neutralized with either zinc or sodium ions (commonly known as ionomers); acrylate and methacrylate polymers and copolymers (e.g., n-butyl methacrylate); acetal polymers and copolymers; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polyamide polymers and copolymers including nylon 6,6, nylon 12, polycaprolactams, polyacrylamides and polyether block amides; polysulfone polymers and copolymers including polyarylsulfones and polyethersulfones; resins including alkyd resins, phenolic resins, urea resins, melamine resins, epoxy resins, allyl resins and epoxide resins; polycarbonates; polyacrylonitriles; polybenzimidazoles; polyesters including polyethylene terephthalates and aliphatic polyester polymers and copolymers of alpha-hydroxy acids such as polylactide (including d-,l- and meso forms), polyglycolide and poly(lactide-co-glycolide), epsilon-caprolactone, poly(lactide-co-caprolactone), polyhydroxybutyrate, polyhydroxyvalerate, poly(para-dioxanone), polymers of trimethylene carbonate (and its alkyl derivatives), 1,4-dioxepan-2-one, 1,5-dioxepan-2-one, and 6,6-dimethyl-1,4-dioxan-2-one; polyether polymers and copolymers including polyarylethers such as polyphenylene ethers, polyether ketones, polyether ether ketones, and polyalkyl oxides such as polyethylene oxide (PEO) and polypropylene oxide; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof, examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; waxes, such as paraffin wax; biopolymers, such as polypeptides, proteins and polysaccharides and fatty acids (and esters thereof), including collagen, dextranomer fibrin, fibrinogen, elastin, chitosan, gelatin, starch, glycosaminoglycans such as hyaluronic acid.

Particularly desirable polymers include polystyrene (and other vinyl aromatic polymers), polymethacrylates and polycarbonates, as well as blends and copolymers containing the same.

In some embodiments, the polymers comprise one or more of the biodisintegrable polymer chains, such as one or more polyester chains selected from poly(glycolic acid), poly(lactic acid), poly(lactic acid-co-glycolic acid), polycaprolactone, polyanhydrides (Polymerix Inc., Piscataway, N.J., USA), PEG-polybutyl terephthalate (SurModics, Inc., Eden Prairie, Minn., USA, IsoTis Orthobiolics, Inc., Irvine, Calif., USA), tyrosine based polyacrylates (TyRx Pharma, Inc., New Brunswick, N.J., USA and Reva Medical, Inc., San Diego, Calif., USA) and polyamide-esters (MediVas LLC, California, USA).

As noted above, the medical devices of the present invention contain one or more therapeutic agents. "Drugs," "therapeutic agents," "pharmaceutically active agents," "pharmaceutically active materials," and other related terms may be used interchangeably herein. These terms include genetic therapeutic agents, non-genetic therapeutic agents and cells.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin; (t) beta-blockers, (u) bARKct inhibitors, (v) phospholamban inhibitors, and (w) Serca 2 gene/protein.

Preferred non-genetic therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors and Serca 2 gene/protein.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SU-PRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including a-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE 1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in connection with the medical devices of the present invention, with the therapeutically effective amount being readily determined by those of ordinary skill in the art and ultimately depending, for example, upon the condition to be treated, the age, sex and condition of the patient, the nature of the therapeutic agent, the nature of the polymeric release region(s), the nature of the medical device, and so forth.

Numerous techniques are available for forming polymeric release regions, which can be subjected to crazing in vivo or ex vivo as discussed above, in accordance with the present invention.

For example, where the polymeric release region is formed from one or more polymers having thermoplastic characteristics, a variety of standard thermoplastic processing techniques can be used to form the polymeric release region, including compression molding, injection molding, blow molding, spinning, vacuum forming and calendaring, as well as extrusion into sheets, fibers, rods, tubes and other cross-sectional profiles of various lengths. Using these and other thermoplastic processing techniques, entire devices or portions thereof can be made.

Solvent-based techniques can also be used to form the polymeric release regions of the present invention. Using these techniques, a polymeric release region can be formed by first providing a solution that contains the polymer(s) for forming the release region. The solvent that is ultimately selected will contain one or more solvent species, which are generally selected based on their ability to dissolve the polymer or polymers that form the polymeric release region, as well as other factors, including drying rate, surface tension, etc. Generally, several solvents will be tested to see which provides polymeric release regions having the best characteristics. Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In some embodiments of the invention, a polymer melt (where thermoplastic processing is employed) or polymer containing solution (where solvent-based processing is employed) is applied to a substrate to form a polymeric release region. For example, the substrate can correspond to all or a portion of an implantable or insertable medical device to which a polymeric release region is applied. The substrate can also be, for example, a template, such as a mold, from which the polymeric release region is removed after solidification. In other embodiments, for example, extrusion and co-extrusion techniques, one or more polymeric release regions are formed without the aid of a substrate.

In a more specific example, an entire stent body is extruded. In another, a polymer release layer is co-extruded along with and underlying stent body. In another, a polymeric layer is provided on an underlying step body by extruding a coating layer onto a pre-existing stent body. In yet another more specific example, a stent is cast in a mold.

If it is desired to provide one or more therapeutic agents and/or other optional agents in the polymeric release region, and so long as these agents are stable under processing conditions, then they can be provided within the polymer melt or polymer containing solution and co-processed along with the polymer(s). Alternatively, therapeutic and/or other optional agents can be introduced subsequent to the formation of the polymeric release region. For instance, in some embodiments, the therapeutic and/or other optional agents are dissolved or dispersed within a solvent, and the resulting solution contacted with a previously formed polymeric release region (e.g., using one or more of the application techniques described above, such as dipping, spraying, etc.). Where the crazing is conducted ex vivo, the solution can be applied before or after creating of the crazing.

As noted above, barrier layers are formed over a therapeutic-agent-containing region in some embodiments of the invention. In these embodiments, a polymeric barrier region can be formed over a therapeutic-agent-containing region, for example, using one of the solvent based or thermoplastic techniques described above. Alternatively, a previously formed polymeric release region can be applied over a therapeutic agent containing region.

Regardless of the technique selected for initially forming the polymeric release region, it is desirable in various embodiments of the invention to form the polymeric release regions under conditions (e.g., highly non-equilibrium conditions) that will provide the polymeric release region with large amounts of residual stress, as it is believed that such residual stress, in turn, enhances the tendency of the polymeric release region to form crazes. For example, where thermoplastic technique are used to form the polymeric regions, fast quenches (e.g., by immersion into a cool medium, such as water) can be employed for this purpose. As another example, where solvent-based processing techniques are used to form the polymeric regions, solvents that lead to fast drying can be employed for this purpose.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable expandable medical device for therapeutic agent release comprising: (a) a polymeric release region that is adapted to undergo crazing as a result of mechanical stresses that are applied during implantation or insertion of the expandable medical device into a patient; and (b) and a therapeutic agent disposed beneath or within said polymeric release region.

2. The implantable or insertable medical device of claim 1, wherein said expandable medical device is selected from a balloon, a stent and a catheter.

3. The implantable or insertable medical device of claim 1, wherein said therapeutic agent is disposed beneath said release region.

4. The implantable or insertable medical device of claim 1, wherein said therapeutic agent is disposed within said release region.

5. The implantable or insertable medical device of claim 1, wherein said therapeutic agent is disposed within said polymeric release region, and wherein said polymeric release region constitutes the bulk of said medical device.

6. The implantable or insertable medical device of claim 5, wherein said polymeric release region is a stent body.

7. The implantable or insertable medical device of claim 1, wherein said polymeric release region is in the form of a polymeric layer.

8. The implantable or insertable medical device of claim 7, wherein said polymeric layer is disposed over a substrate.

9. The implantable or insertable medical device of claim 8, wherein said polymeric layer is disposed over a region comprising said therapeutic agent.

10. The implantable or insertable medical device of claim 8, wherein said therapeutic agent is disposed within said polymeric layer.

11. The implantable or insertable medical device of claim 1, wherein said polymeric release region is in the form of a fiber.

12. The implantable or insertable medical device of claim 1, wherein said therapeutic agent is selected from anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

13. The implantable or insertable medical device of claim 1, wherein medical device comprises a plurality of different therapeutic agents.

14. The implantable or insertable medical device of claim 1, where said polymeric release region is formed by evaporation of solvent from a fluid comprising said solvent and dissolved polymer.

15. The implantable or insertable medical device of claim 1, wherein said polymeric release region is formed from a polymer melt.

16. The implantable or insertable medical device of claim 1, wherein said polymeric release region comprises a polymer selected from polymethacrylates, polycarbonates, and copolymers comprising the same.

17. The implantable or insertable medical device of claim 1, wherein said polymeric release region comprises a vinyl aromatic polymer.

18. The implantable or insertable medical device of claim 1, wherein said polymeric release region comprises a polymer selected from polystyrene and a copolymer comprising polystyrene.

19. The implantable or insertable medical device of claim 1, wherein said polymeric release region comprises a polymer comprising a biodisintegrable polymer chain.

20. The implantable or insertable medical device of claim 1, wherein said polymeric release region is in the form of a balloon coating or a stent coating.

21. An implantable or insertable medical device for therapeutic agent release comprising: (a) a polymeric release region that contains crazing, said polymeric release region comprising a vinyl aromatic polymer; and (b) and a therapeutic agent disposed beneath or within said polymeric release region, wherein said crazing is formed ex vivo by a method that comprises applying mechanical stress to induce said crazing, applying thermal stress to induce said crazing, or swelling the polymeric release region with a chemical medium to induce crazing.

22. The implantable or insertable medical device of claim 21, wherein said medical device is selected from a guide wire, a balloon, a catheter, a vena cava filter, a stent, a stent graft, a vascular graft, a cerebral aneurysm filler coil, a myocardial plug, a heart valve, a vascular valve, and a tissue engineering scaffold.

23. The implantable or insertable medical device of claim 21, wherein said therapeutic agent is disposed beneath said release region.

24. The implantable or insertable medical device of claim 21, wherein said therapeutic agent is disposed within said release region.

25. The implantable or insertable medical device of claim 21, wherein said therapeutic agent is disposed within said polymeric release region, and wherein said polymeric release region constitutes the bulk of said medical device.

26. The implantable or insertable medical device of claim 25, wherein said polymeric release region is a stent body.

27. The implantable or insertable medical device of claim 21, wherein said polymeric release region is in the form of a polymeric layer.

28. The implantable or insertable medical device of claim 27, wherein said polymeric layer is disposed over a substrate.

29. The implantable or insertable medical device of claim 28, wherein said polymeric layer is disposed over a region comprising said therapeutic agent.

30. The implantable or insertable medical device of claim 28, wherein said therapeutic agent is disposed within said polymeric layer.

31. The implantable or insertable medical device of claim 21, wherein said polymeric release region is in the form of a fiber.

32. The implantable or insertable medical device of claim 21, wherein said therapeutic agent is selected from anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

33. The implantable or insertable medical device of claim 21, wherein said medical device comprises a plurality of different therapeutic agents.

34. The implantable or insertable medical device of claim 21, where said polymeric release region is formed by evaporation of solvent from a fluid comprising said solvent and dissolved polymer.

35. The implantable or insertable medical device of claim 21, wherein said polymeric release region is formed from a polymer melt.

36. The implantable or insertable medical device of claim 35, wherein said polymer melt is cooled by a process comprising a quenching step.

37. The implantable or insertable medical device of claim 21, wherein said polymeric release region comprises a polymer selected from polystyrene and a copolymer comprising polystyrene.

38. The implantable or insertable medical device of claim 21, wherein said polymeric release region comprises a polymer comprising a biodisintegrable polymer chain.

* * * * *

UNITED STATES PATENT AND TRADEMARK OFFICE
CERTIFICATE OF CORRECTION

| | | |
|---|---|---|
| PATENT NO. | : 7,988,987 B2 | Page 1 of 1 |
| APPLICATION NO. | : 11/042038 | |
| DATED | : August 2, 2011 | |
| INVENTOR(S) | : Shrirang V. Ranade | |

It is certified that error appears in the above-identified patent and that said Letters Patent is hereby corrected as shown below:

col. 3, line 35, after "that" remove "that".

col. 3, line 64, after "expected" insert --to--.

col. 5, line 28, after "is" insert --a--.

col. 7, line 37, after "4-bromostyrene" change "(Tg -18°C)" to --(Tg -118°C)--.

col. 8, line 4, after "methacrylate" change "(Tg -100°C)" to --(Tg -110°C)--.

col. 8, lines 19-20, after "acrylate" change "(Tg -110°C)" to --(Tg -10°C)--.

Signed and Sealed this
Thirteenth Day of March, 2012

David J. Kappos
*Director of the United States Patent and Trademark Office*